US012593741B2

(12) United States Patent
Schroeder

(10) Patent No.: US 12,593,741 B2
(45) Date of Patent: Apr. 7, 2026

(54) AGRICULTURAL SYSTEM AND METHOD FOR MONITORING FIELD CHARACTERISTICS OF A FIELD

(71) Applicant: CNH Industrial America LLC, New Holland, PA (US)

(72) Inventor: Brittany Schroeder, Bunker Hill, IN (US)

(73) Assignee: CNH Industrial America LLC, New Holland, PA (US)

( * ) Notice: Subject to any disclaimer, the term of this patent is extended or adjusted under 35 U.S.C. 154(b) by 824 days.

(21) Appl. No.: 17/949,771

(22) Filed: Sep. 21, 2022

(65) Prior Publication Data

US 2024/0090362 A1 Mar. 21, 2024

(51) Int. Cl.
*A01B 79/00* (2006.01)
*G01N 27/72* (2006.01)
(Continued)

(52) U.S. Cl.
CPC ........... *A01B 79/005* (2013.01); *G01N 27/72* (2013.01); *G01N 33/24* (2013.01); *G01S 13/885* (2013.01); *G01N 33/245* (2024.05)

(58) Field of Classification Search
CPC ...... A01B 79/005; A01B 79/00; G01N 27/72; G01N 27/00; G01N 33/00; G01N 33/245; (Continued)

(56) References Cited

U.S. PATENT DOCUMENTS 6,826,894 B2 12/2004 Thiemann et al.
8,688,331 B2 4/2014 Peterson et al.
(Continued)

FOREIGN PATENT DOCUMENTS

CN 112956289 B 10/2021
DE 102008005191 A1 7/2008
(Continued)

OTHER PUBLICATIONS

Marlowe Edgar Burce, et al. "Development of Seeding Depth Control System for Conservation Tillage Cultivation" Journal of JSAM 76(1): 62~69, 2014 (8 pages) https://www.istage.jst.jp/article/jsamfe/76/1/76_62/_pdf.
(Continued)

*Primary Examiner* — Christopher J. Novosad
(74) *Attorney, Agent, or Firm* — Dority & Manning. P.A.

(57) ABSTRACT

An agricultural system includes a vehicle configured to perform one or more passes across a field, and a field characteristics sensor supported on the vehicle, spaced apart from a surface of the field during the one or more passes, with the field characteristics sensor being configured to generate data indicative of at least one characteristic of the field below the surface of the field. Further, the agricultural system includes an actuator selectively controllable to move the field characteristics sensor relative to the vehicle. Moreover, the agricultural system includes at least one distance sensor supported on the vehicle and configured to generate distance data indicative of a distance between the field characteristics sensor and the surface of the field. Additionally, the agricultural system includes a computing system configured to receive the distance data and initiate a control action based at least in part on the distance data.

20 Claims, 4 Drawing Sheets

(51) Int. Cl.
  *G01N 33/24* (2006.01)
  *G01S 13/88* (2006.01)
(58) Field of Classification Search
  CPC ....... G01N 33/24; G01S 13/885; G01S 13/88;
    G01S 13/00
  See application file for complete search history.

(56) References Cited

U.S. PATENT DOCUMENTS

| | | | |
|---|---|---|---|
| 8,843,283 | B2 | 9/2014 | Strelioff et al. |
| 9,510,508 | B2 | 12/2016 | Jung |
| 9,832,926 | B2 | 12/2017 | Jung et al. |
| 10,973,171 | B2 | 4/2021 | Smith et al. |
| 11,076,532 | B2 | 8/2021 | Seiders, Jr. |
| 11,172,613 | B2 | 11/2021 | Weitenberg et al. |
| 2018/0027727 | A1 | 2/2018 | Leeb |
| 2020/0341117 | A1* | 10/2020 | Sandford ................ G01S 17/93 |
| 2020/0359542 | A1 | 11/2020 | Bögel et al. |
| 2021/0105931 | A1 | 4/2021 | Anderson, Jr. et al. |
| 2021/0120725 | A1 | 4/2021 | Seiders, Jr. |
| 2021/0127576 | A1 | 5/2021 | Seiders, Jr. |
| 2021/0185879 | A1 | 6/2021 | Hunt et al. |
| 2021/0315147 | A1 | 10/2021 | Fanshier et al. |
| 2022/0076387 | A1 | 3/2022 | Rees |

FOREIGN PATENT DOCUMENTS

| | | | | |
|---|---|---|---|---|
| FR | 3002664 | A1 * | 8/2014 | ........ G06F 13/4068 |
| WO | WO2021/242867 | A1 | 12/2021 | |

OTHER PUBLICATIONS

University of Nebraska-Lincoln Institute of Agricultural and Natural Resources Cropwatch "Soil and Crop Sensing" 2022 (5 pages) https://cropwatch.unl.edu/ssm/sensing.
Tanja Folnović "Smart Sensors for Accurate Soil Measurements" Farm Business (11 pages) https://www.agrivi.com/blog/smart-sensors-for-accurate-soil-measurements/.
R. Sui, et al. "Ground-Based Sensing System for Cotton Nitrogen Status Determination" vol. 49(6): 1983-1991 2006 American Society of Agricultural and Biological Engineers ISSN 0001-2351 (9 pages) https://scihub.hkvisa.net/10.13031/2013.22279.

* cited by examiner

300

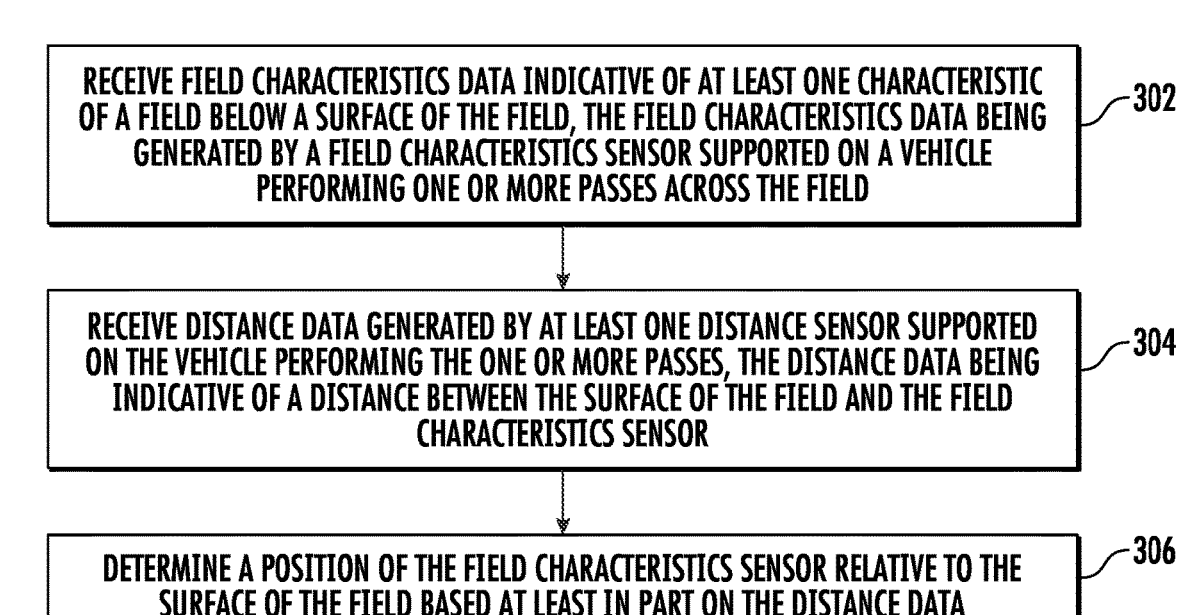

| | |
|---|---|
| RECEIVE FIELD CHARACTERISTICS DATA INDICATIVE OF AT LEAST ONE CHARACTERISTIC OF A FIELD BELOW A SURFACE OF THE FIELD, THE FIELD CHARACTERISTICS DATA BEING GENERATED BY A FIELD CHARACTERISTICS SENSOR SUPPORTED ON A VEHICLE PERFORMING ONE OR MORE PASSES ACROSS THE FIELD | 302 |
| RECEIVE DISTANCE DATA GENERATED BY AT LEAST ONE DISTANCE SENSOR SUPPORTED ON THE VEHICLE PERFORMING THE ONE OR MORE PASSES, THE DISTANCE DATA BEING INDICATIVE OF A DISTANCE BETWEEN THE SURFACE OF THE FIELD AND THE FIELD CHARACTERISTICS SENSOR | 304 |
| DETERMINE A POSITION OF THE FIELD CHARACTERISTICS SENSOR RELATIVE TO THE SURFACE OF THE FIELD BASED AT LEAST IN PART ON THE DISTANCE DATA | 306 |
| INITIATE A CONTROL ACTION BASED AT LEAST IN PART ON THE POSITION OF THE FIELD CHARACTERISTICS SENSOR RELATIVE TO THE SURFACE OF THE FIELD | 308 |

FIG. 4

AGRICULTURAL SYSTEM AND METHOD FOR MONITORING FIELD CHARACTERISTICS OF A FIELD

FIELD OF THE INVENTION

The present disclosure relates generally to performing one or more passes across a field with an agricultural vehicle, and, more particularly, to monitoring field characteristics below a surface of the field during the one or more passes using non-contact sensors.

BACKGROUND OF THE INVENTION

It is well known that, to attain the best agricultural performance from a piece of land, a farmer must cultivate the soil, typically through a tillage operation. Common tillage operations include plowing, harrowing, and subsoiling. Modern farmers perform these tillage operations by pulling a tillage implement behind an agricultural work vehicle, such as a tractor. Depending on the crop selection and the soil conditions, a farmer may need to perform several tillage operations at different times over a crop cycle to properly cultivate the land to suit the crop choice.

When performing certain tillage operations, it is generally desirable to break up any layers of subsurface soil that have been compacted (e.g., due to vehicle traffic, ponding, and/or the like). As such, during such tillage operations, shanks or other ground-penetrating tools supported on the tillage implement are pulled through the soil to fracture the compaction layer. However, the depth of the compaction layer and other field characteristics, such as moisture content, may vary throughout the field. In this respect, sensing systems have been developed that have sensors that allow compaction layers and other field characteristics to be detected without contacting the ground such that the penetration depths of the shanks or other tools may be adjusted accordingly. While such systems work well, further improvements are needed. Particularly, certain non-contact sensors of the sensing system need to be kept at a certain orientation (e.g., distance and angle) relative to the surface of the field in order to be able to accurately determine field characteristics below the surface of the field. Manually adjusting the sensing system can be time consuming and may not sufficiently account for variations in the terrain.

Accordingly, an improved agricultural system and method for monitoring field characteristics within a field, particularly below a surface of the field, would be welcomed in the technology.

BRIEF DESCRIPTION OF THE INVENTION

Aspects and advantages of the invention will be set forth in part in the following description, or may be obvious from the description, or may be learned through practice of the invention.

In one aspect, the present subject matter is directed to an agricultural system for monitoring field characteristics of a field. The agricultural system may include a vehicle configured to perform one or more passes across a field. The agricultural system may further include a field characteristics sensor supported on the vehicle such that the field characteristics sensor is spaced apart from a surface of the field during the one or more passes across the field, with the field characteristics sensor being configured to generate field characteristics data indicative of at least one characteristic of the field below the surface of the field. Further, the agricultural system may include a sensor actuator coupled between the field characteristics sensor and the vehicle, where the sensor actuator is selectively controllable to move the field characteristics sensor relative to the vehicle. Moreover, the agricultural system may include at least one distance sensor supported on the vehicle, with the at least one distance sensor being configured to generate distance data indicative of a distance between the field characteristics sensor and the surface of the field. Additionally, the agricultural system may include a computing system configured to receive the distance data and initiate a control action based at least in part on the distance data.

In another aspect, the present subject matter is directed to an agricultural method for monitoring field characteristics of a field. The agricultural method may include receiving, with a computing device, field characteristics data indicative of at least one characteristic of a field below a surface of the field, where the field characteristics data is generated by a field characteristics sensor supported on a vehicle performing one or more passes across the field. Further, the agricultural method may include receiving, with the computing device, distance data generated by at least one distance sensor supported on the vehicle performing the one or more passes, with the distance data being indicative of a distance between a surface of the field and the field characteristics sensor. Moreover, the agricultural method may include determining, with the computing device, a position of the field characteristics sensor relative to the surface of the field based at least in part on the distance data. Additionally, the agricultural method may include initiating, with the computing device, a control action based at least in part on the position of the field characteristics sensor relative to the surface of the field.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 4 illustrates a flow diagram of one embodiment of a method for monitoring field characteristics within a field in accordance with aspects of the present subject matter.

Figure 1:
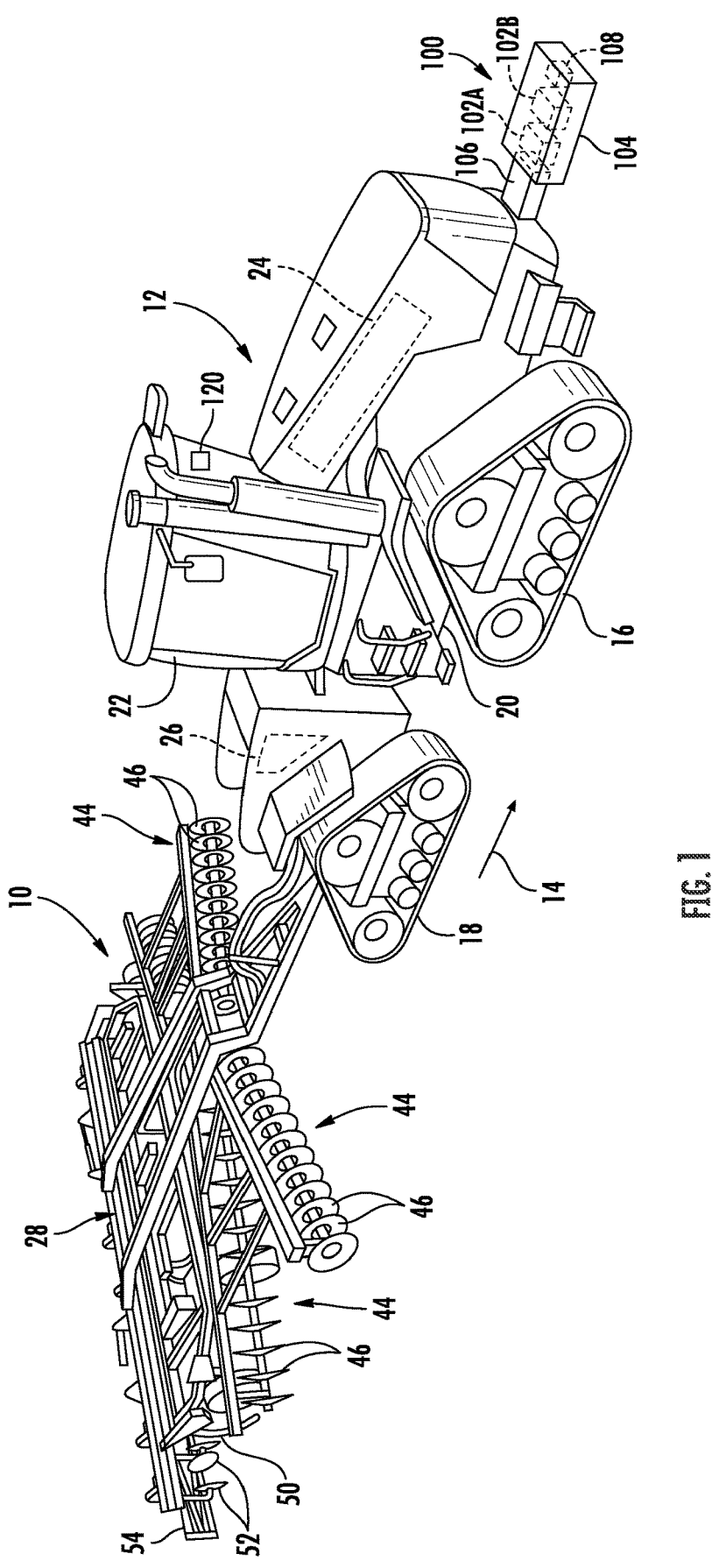
FIG. 1 illustrates a perspective view of one embodiment of a tillage implement coupled to a work vehicle in accordance with aspects of the present subject matter.

Repeat use of reference characters in the present specification and drawings is intended to represent the same or analogous features or elements of the present technology.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to agricultural systems and methods for monitoring field characteristics of a field during one or more passes across a field. Specifically, the disclosed system may include one or more field characteristics sensors configured to generate field characteristics data indicative of at least one characteristic of the field below the surface of the field (e.g., hard pan layer depth, moisture content, etc.). Particularly, the field characteristics sensor(s) is supported on an agricultural vehicle such that the field characteristics sensor(s) is spaced apart from a surface of a field during the one or more passes across the field with the agricultural vehicle. In some instances, the field characteristics sensor(s) includes a ground penetrating radar (GPR), an electromagnetic induction (EMI) sensor, and/or the like. The field characteristics sensor(s) may be supported such that it is movable relative to the vehicle by a sensor actuator(s). The field characteristics sensor(s) needs to be within a certain operating orientation (e.g., distance and/or angle) relative to the surface of the field to accurately collect data. However, the field characteristics sensor(s) may be spaced apart from the vehicle along (e.g., along a direction of travel or laterally), such that the field characteristics sensor(s) is not always kept at the correct orientation relative to the surface of the field as the vehicle performs the one or more passes.

Thus, in accordance with aspects of the present subject matter, the disclosed system may also include a distance sensor(s) configured to generate distance data indicative of the distance between the field characteristics sensor(s) and the surface of the field. The distance sensor(s) may be a laser line sensor, an infrared sensor, an ultrasonic sensor, a LIDAR sensor, a radar sensor, and/or the like. Based on the distance data, a computing system of the disclosed system may be configured to determine the position or orientation (e.g., distance and/or angle) of the field characteristics sensor(s) relative to the surface of the field, and to initiate a control action based on the orientation. For instance, in some embodiments, the computing system may automatically control the sensor actuator(s) to keep the field characteristics sensor(s) at the correct orientation relative to the surface of the field. In one embodiment, the computing system may control a user interface to indicate the orientation of the field characteristics sensor(s) relative to the surface of the field. As such, the disclosed system and method allow for the position or orientation of the field characteristics sensor(s) to be automatically monitored and for control actions to be performed based on the position/orientation, both of which increase the accuracy of the field characteristic data collected with such field characteristic sensor(s) while reducing the amount of time it takes to keep the field characteristics sensor(s) at the correct orientation relative to the surface of the field.

Figure 2:
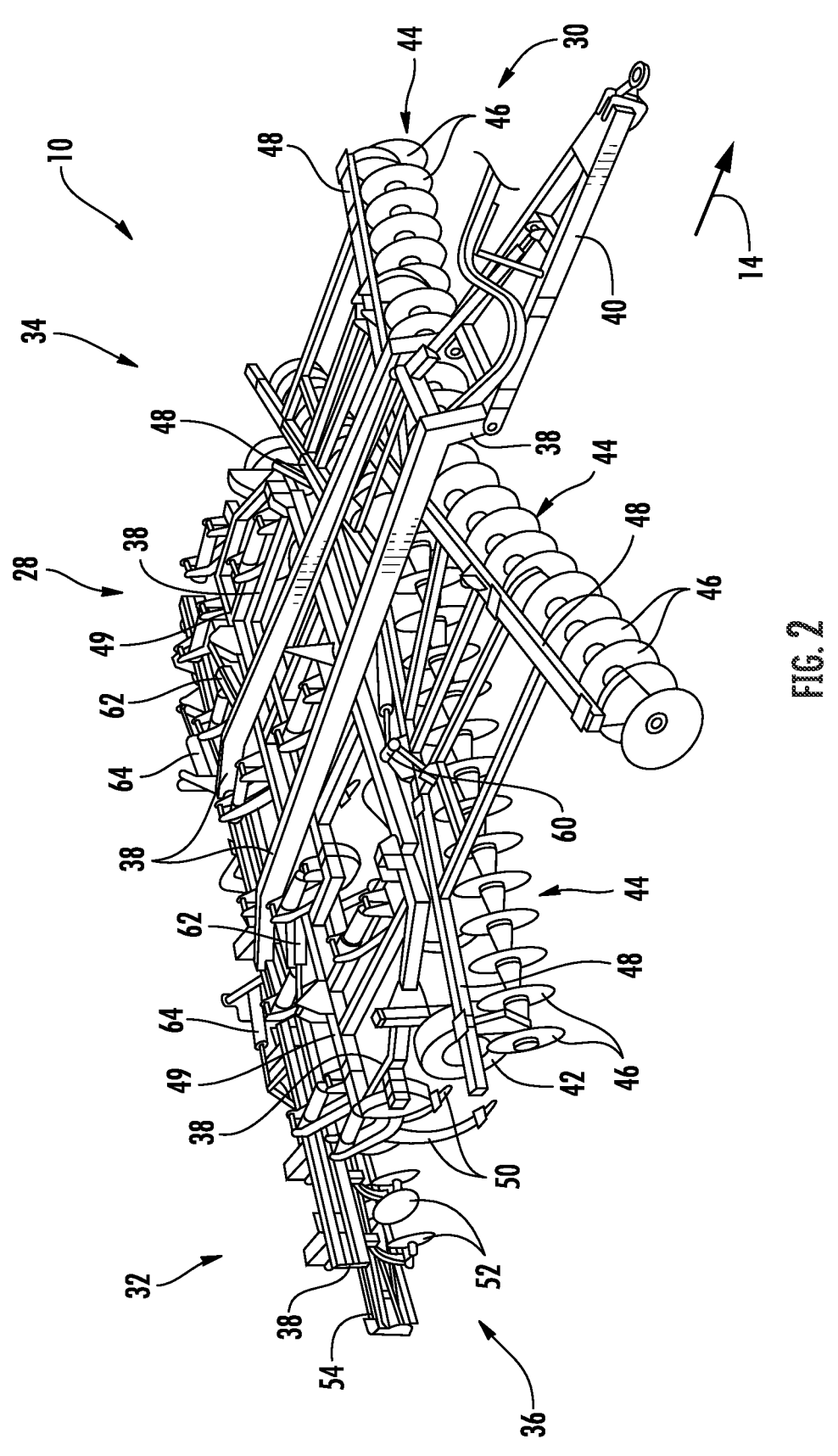
FIG. 2 illustrates another perspective view of the implement, particularly illustrating various components of the implement, in accordance with aspects of the present subject matter.

Referring now to the drawings, FIGS. 1 and 2 illustrate differing perspective views of one embodiment of an agricultural implement 10 in accordance with aspects of the present subject matter. Specifically, FIG. 1 illustrates a perspective view of the agricultural implement 10 coupled to a work vehicle 12. Additionally, FIG. 2 illustrates a perspective view of the implement 10, particularly illustrating various components of the implement 10.

In general, the implement 10 may be configured to be towed across a field in a direction of travel (e.g., as indicated by arrow 14) by the work vehicle 12. As shown, the implement 10 may be configured as a tillage implement, and the work vehicle 12 may be configured as an agricultural tractor. However, in other embodiments, the implement 10 may be configured as any other suitable type of implement, such as a seed-planting implement, a fertilizer-dispensing implement, and/or the like. Similarly, the work vehicle 12 may be configured as any other suitable type of vehicle, such as an agricultural harvester, a self-propelled sprayer, and/or the like.

As shown in FIG. 1, the work vehicle 12 may include a pair of front track assemblies 16, a pair or rear track assemblies 18, and a frame or chassis 20 coupled to and supported by the track assemblies 16, 18. An operator's cab 22 may be supported by a portion of the chassis 20 and may house various input devices (e.g., one or more user interfaces 120) for permitting an operator to control the operation of one or more components of the work vehicle 12 and/or one or more components of the implement 10. Additionally, as is generally understood, the work vehicle 12 may include an engine 24 and a transmission 26 mounted on the chassis 20. The transmission 26 may be operably coupled to the engine 24 and may provide variably adjusted gear ratios for transferring engine power to the track assemblies 16, 18 via a drive axle assembly (not shown) (or via axles if multiple drive axles are employed).

As shown in FIGS. 1 and 2, the implement 10 may include a frame 28. More specifically, as shown in FIG. 2, the frame 28 may extend longitudinally between a forward end 30 and an aft end 32. The frame 28 may also extend laterally between a first side 34 and a second side 36. In this respect, the frame 28 generally includes a plurality of structural frame members 38, such as beams, bars, and/or the like, configured to support or couple to a plurality of components. Furthermore, a hitch assembly 40 may be connected to the frame 28 and configured to couple the implement 10 to the work vehicle 12. Additionally, a plurality of wheels 42 (only one of which is shown in FIG. 2) may be coupled to the frame 28 to facilitate towing the implement 10 in the direction of travel 14.

In several embodiments, one or more ground engaging tools may be coupled to and/or supported by the frame 28. In such embodiments, the ground engaging tool(s) may, for example, include one or more ground-penetrating tools. More particularly, in certain embodiments, the ground engaging tools may include one or more disk blades 46 and/or one or more shanks 50 supported relative to the frame 28. In one embodiment, each disk blade 46 and/or shank 50 may be individually supported relative to the frame 28. Alternatively, one or more groups or sections of the ground engaging tools may be ganged together to form one or more ganged tool assemblies, such as the disk gang assemblies 44 shown in FIGS. 1 and 2.

As illustrated in FIG. 2, each disk gang assembly 44 includes a toolbar 48 coupled to the implement frame 28 and a plurality of disk blades 46 supported by the toolbar 48 relative to the implement frame 28. Each disk blade 46 may, in turn, be configured to penetrate into or otherwise engage the soil as the implement 10 is being pulled through the field. As is generally understood, the various disk gang assemblies 44 may be oriented at an angle relative to the direction of travel 14, such that an axis of rotation of the disks is not perpendicular to the direction of travel 14, to promote more effective tilling of the soil. However, it should be appreciated that the disk gang assemblies 44 may be oriented in any other suitable manner relative to the direction of travel 14. In the embodiment shown in FIGS. 1 and 2, the implement 10 includes four disk gang assemblies 44 supported on the frame 28 at a location forward of the shanks 50, adjacent to the forward end 30 of the implement 10, such as by including two forward disk gang assemblies 44 and two rear disk gang assemblies 44. However, it should be appreciated that, in alternative embodiments, the implement 10 may include any other suitable number of disk gang assemblies 44, such as more or fewer than four disk gang assemblies 44. Furthermore, in one embodiment, the disk gang assemblies 44 may be mounted to the frame 28 at any other suitable location, such as adjacent to aft end 32 of the implement 10.

It should be appreciated that, in addition to the shanks 50 and the disk blades 46, the implement frame 28 may be configured to support any other suitable ground engaging tools. For instance, in the illustrated embodiment, the frame 28 is also configured to support a plurality of leveling blades 52 and rolling (or crumbler) basket assemblies 54.

Moreover, in several embodiments, the implement 10 may include a plurality of actuators configured to adjust the positions of the implement 10 and/or various ground engaging tools coupled thereto. For example, in some embodiments, the implement 10 may include a plurality of disk gang actuators 60 (one is shown in FIG. 2), with each actuator 60 being configured to move or otherwise adjust the orientation or position of one or more of the disk gang assemblies 44 relative to the implement frame 28. For example, a first end of each actuator 60 may be coupled to a toolbar 48 of the corresponding disk gang assembly 44, while a second end of each actuator 60 may be coupled to the frame 28. Each actuator 60 may be configured to extend and/or retract to adjust the angle of the corresponding disk gang assembly(ies) 44 relative to a lateral centerline (not shown) of the frame 28 and/or the penetration depth of the associated disk blades 46. Furthermore, each actuator 60 may be configured to extend and/or retract to adjust a downforce applied by the actuator(s) 60 to the disk gang assembly(ies) 44, and thus the disk blades 46.

Further, in some embodiments, the implement 10 may include a plurality of shank frame actuator(s) 62 (FIG. 2), with each actuator 62 being configured to move or otherwise adjust the orientation or position of one or more of the shanks 50 relative to the implement frame 28. For example, each actuator 62 may be coupled between a toolbar 49 supporting the shank(s) 50 and the implement frame 28. As such the actuator(s) 62 may be configured to extend and/or retract to adjust the position of the toolbar(s) 49 and, thus, a penetration depth of the associated shank(s) 50. Similarly, in some embodiments, the implement 10 may include a plurality of basket actuator(s) 64, with each actuator 64 being configured to move or otherwise adjust the orientation or position of one or more of the basket assemblies 54 relative to the implement frame 28. For example, each actuator 64 may be coupled between one or more of the basket assemblies 54 and the implement frame 28 and be configured to extend and/or retract to adjust an aggressiveness of the associated basket assembly(ies) 54.

In the illustrated embodiment, each actuator 60, 62, 64 corresponds to a fluid-driven actuator, such as a hydraulic or pneumatic cylinder. However, it should be appreciated that each actuator 60, 62, 64 may correspond to any other suitable type of actuator, such as an electric linear actuator.

It should additionally be appreciated that the implement 10 may include any other suitable actuators for adjusting the position and/or orientation of the ground-engaging tools of the implement 10 relative to the ground and/or implement frame 28.

In accordance with aspects of the present subject matter, the implement 10 and/or the work vehicle 12 may be equipped with different types of sensors for monitoring different conditions during the performance of one or more passes of a field (e.g., during an agricultural operation with the implement 10). For instance, at least one sensor assembly 100 may be supported on the work vehicle 12 and/or on the implement 10. The sensor assembly(ies) 100 may include at least one field characteristics sensor configured to generate data indicative of a field characteristic (e.g., soil moisture content, depth of compaction layer, etc.) below a surface of the field. For example, in some embodiments, the sensor assembly 100 includes a first field characteristic sensor 102A and a second field characteristic sensor 102B. The field characteristics sensors 102A, 102B may be different types of non-contact sensors configured to generate field characteristics data indicative of the field characteristic(s) below the surface of the field while being spaced apart from the surface of the field. For instance, the first field characteristic sensor 102A may be a ground penetrating radar (GPR), while the second field characteristic sensor 102B may be an electromagnetic induction (EMI) sensor. However, it should be appreciated that the field characteristics sensors 102A, 102B may be any other suitable combination of sensors. It should also be appreciated that, in some embodiments, the sensor assembly 100 includes only one of the field characteristics sensors 102A, 102B, or includes additional field characteristics sensors.

In one embodiment, the field characteristics sensors 102A, 102B of each sensor assembly 100 are supported on a common housing 104 of the respective sensor assembly 100. In one embodiment, the sensor assembly 100 may be positioned such that the field characteristics may be determined based on the data generated by the field characteristics sensor(s) 102A, 102B before the implement 10 has finished passing over the given location. For example, as shown in FIG. 1, in one embodiment, the housing 104 is supported at a front end of the work vehicle 12 relative to the direction of travel 14, extending forward of the work vehicle 12. However, in other embodiments, the housing 104 may be supported at a rear end of the work vehicle 12, and/or at a front end of the implement 10. Further, in some embodiments, the housing 104 may extend laterally from the work vehicle 12 and/or the implement 10. The housing 104 being movably supported relative to the vehicle 12 and/or the implement 10 by at least one sensor actuator 106 of the respective sensor assembly 100. The sensor actuator(s) 106 may be selectively controllable to adjust an orientation of the field characteristics sensors 102A, 102B relative to vehicle 12 and/or the implement 10, and thus, the surface of the field. For instance, the sensor actuator(s) 106 may be controllable to raise and lower and/or rotate the field characteristics sensors 102A, 102B relative to the vehicle 12 and/or the implement 10. In some embodiments, the field characteristics sensors 102A, 102B are at least partially housed within the housing 104. However, it should be appreciated that, in other embodiments, the field characteristics sensors 102A, 102B may be otherwise supported on the housing 104. Moreover, it should be appreciated that, the field characteristics sensors 102A, 102B may be otherwise movably supported relative to the vehicle 12 and/or the implement 10. For instance, the field characteristics sensors 102A, 102B may be separately supported relative to the vehicle 12 and/or the implement 10 such that they are independently movable relative to the vehicle 12 and/or the implement 10. Additionally, it should be appreciated that, while the housing 104 is shown as being directly supported relative to the vehicle 12 by the sensor actuator(s) 106, one or more intermediate elements (e.g., a linkage, a frame, and/or the like) may be positioned between the sensor actuator(s) 106 and the vehicle 12 and/or between the housing 104 and the sensor actuator(s) 106.

In general, the field characteristics sensor(s) 102A, 102B need to be kept at a certain orientation relative to the surface of the field in order to accurately generate field characteristic data. For instance, in some embodiments, the field characteristics sensor(s) 102A, 102B need to be kept within a certain distance range (e.g., less than a first distance threshold and greater than a second distance threshold, the second distance threshold being less than the first distance threshold) from the surface of the field. When the field characteristics sensor(s) 102A, 102B are spaced apart from the work vehicle 12 and/or the implement 10 along the direction of travel 14 and/or laterally, the field characteristics sensor(s) 102A, 102B may not be kept at the proper orientation relative to the surface of the field by the movement of the vehicle 12 and/or the implement 10 across the field. For instance, when the field characteristics sensor(s) 102A, 102B are forward of the work vehicle 12 along the direction of travel 14, the field characteristics sensor(s) 102A, 102B may encounter a slope before the work vehicle 12, which means that the distance between the field characteristics sensor(s) 102A, 102B and the surface of the field changes. Similarly, if the field characteristics sensor(s) 102A, 102B extend laterally outwardly from the work vehicle 12, the field characteristics sensor(s) 102A, 102B may pass across slopes that the wheels of the work vehicle 12 are not subject to, thus changing the distance between the field characteristics sensor(s) 102A, 102B and the surface of the field.

Thus, in accordance with aspects of the present subject matter, the sensor assembly 100 may also include at least one distance sensor 108 configured to generate distance data indicative of a distance between the field characteristics sensor(s) 102A, 102B and the surface of the field. For instance, in one embodiment, the distance sensor 108 may also be supported on the housing 104. In some embodiments, the distance sensor 108 is at least partially enclosed within the housing 104. However, it should be appreciated that, in other embodiments, the distance sensor 108 may be supported on the housing 104 in any other suitable way and/or may positioned at any other suitable location on the vehicle 12 and/or the implement 10. Preferably, in some embodiments, the distance sensor is also a non-contact sensor such that the sensor assembly 100 does not disturb the surface of the field. For example, the distance sensor 108 may include at least one of a laser line sensor, an infrared sensor, an ultrasonic sensor, a LIDAR sensor, or a radar sensor. However, in other embodiments, the distance sensor may be a contact sensor. As will be described in greater detail below, the distance data may be used to control the sensor actuator(s) 106 to maintain the field characteristics sensor(s) 102A, 102B at the desired orientation relative to the surface of the field for generating the field characteristics data accurately.

Similarly, in one embodiment, the field characteristics sensor(s) 102A, 102B need to be kept within a certain angle range relative to the surface of the field (e.g., within +/−100 of parallel, such as within +/−5° of parallel, and/or the like from the surface of the field) such that the field characteristics sensor(s) 102A, 102B are substantially parallel to the surface of the field. Thus, depending on the type of distance sensor(s) 108 used, in some embodiments, the sensor assembly 100 includes at least two of the distance sensors 108 such that the angular orientation of the field characteristics sensor (s) 102A, 102B relative to the surface of the field may be monitored. However, in some embodiments, depending on the type of distance sensor 108 used, only one distance sensor 108 is needed to also determine the angular orientation of the field characteristics sensor(s) 102A, 102B relative to the surface of the field.

In some embodiments, the distance sensor(s) 108 may further be configured to generate data indicative of at least one field characteristic. For instance, when the distance sensor(s) 108 is configured as a radar sensor, the distance sensor(s) 108 may be configured to generate data indicative of coverage and/or thickness of a residue layer on the surface of the field. Particularly, in situations where the particular type of the sensor(s) 102A, 102B is affected by residue layer thickness, knowing the residue layer thickness from the data generated by the distance sensor(s) 108 could be used to improve analysis of the data generated by the field characteristics sensor(s) 102A, 102B. For instance, the data generated by the field characteristics sensor(s) 102A, 102B corresponding to the residue layer determined based at least in part on the data generated by the distance sensor(s) 108 may be ignored, areas with thicker residue determined based at least in part on the data generated by the distance sensor(s) 108 may be weighted less, and/or the like. For example, certain frequencies of ground penetrating radar may be more affected by thicker residue layers, which may lead to less accurate results. As such, adjusting the data generated at particular frequencies of ground penetrating radar may improve the accuracy of the field characteristic monitoring.

It should be appreciated that the configuration of the implement 10 described above and shown in FIGS. 1 and 2 and the work vehicle 12 described above and shown in FIG. 1 is provided only to place the present subject matter in an exemplary field of use. Thus, it should be appreciated that the present subject matter may be readily adaptable to any manner of implement and work vehicle configurations.

Figure 3:
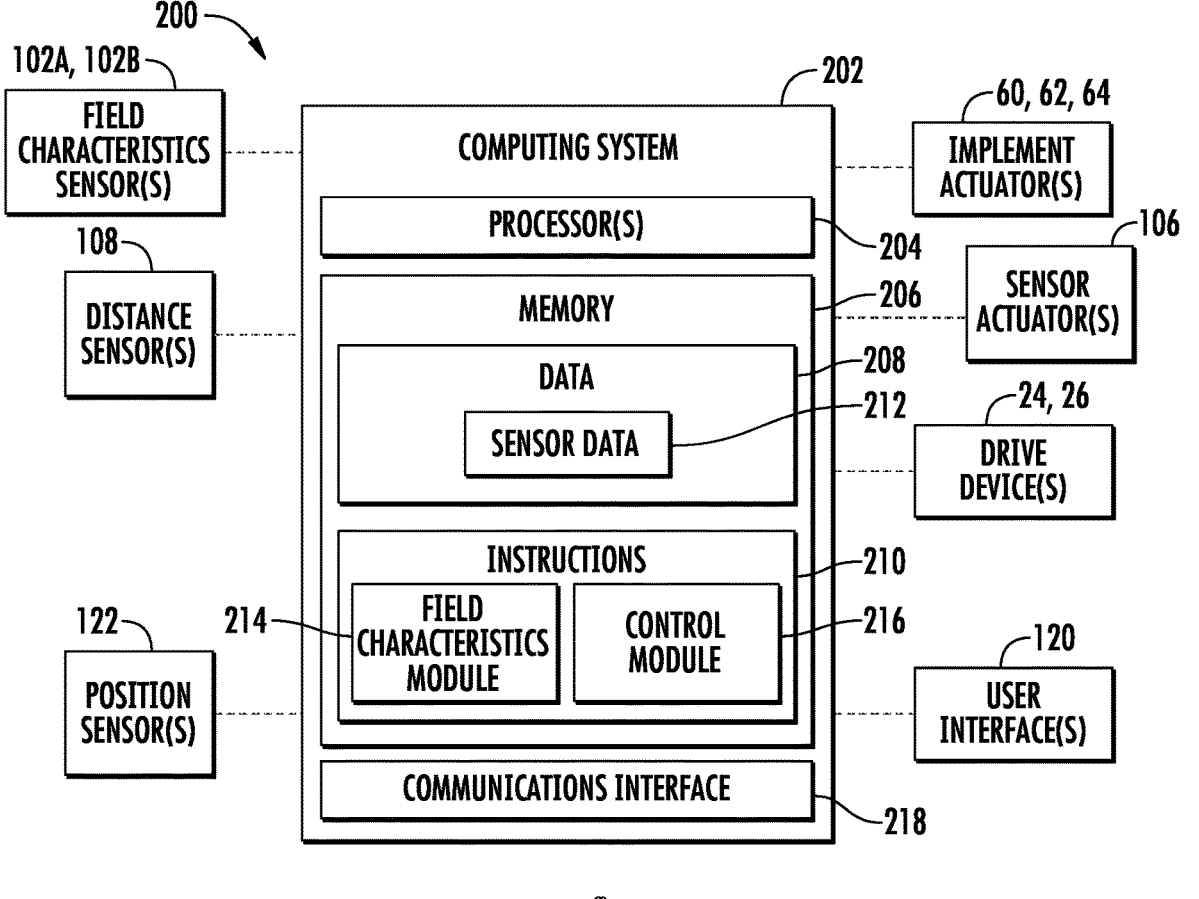
FIG. 3 illustrates a schematic view of a system for monitoring field characteristics within a field in accordance with aspects of the present subject matter.

Referring now to FIG. 3, a schematic view is illustrated of one embodiment of a system 200 for monitoring field characteristics of a field. In general, the system 200 will be described herein with reference to the implement 10 and vehicle 12 described above with reference to FIGS. 1 and 2. However, it should be appreciated that the disclosed system 200 may generally be utilized with any other suitable implement/vehicle combination having any other suitable implement/vehicle configuration. Additionally, it should be appreciated that, for purposes of illustration, communicative links or electrical couplings of the system 200 shown in FIG. 3 are indicated by dashed lines.

In several embodiments, the system 200 may include a computing system 202 and various other components configured to be communicatively coupled to and/or controlled by the computing system 202, such as the field characteristics sensor(s) 102A, 102B configured to generate field data indicative of field characteristics (e.g., soil moisture content, compaction layer depth, and/or the like) within the field, the sensor actuator(s) 106 selectively controllable to adjust an orientation of the field characteristics sensor(s) 102A, 102B relative to the surface of the field, the distance sensor(s) 108 configured to generate distance data indicative of the distance between the field characteristics sensor(s) 102A, 102B and the surface of the field, actuator(s) of the implement 10 (e.g., implement actuator(s) 60, 62, 64), drive device(s) of the vehicle 12 (e.g., engine 24, transmission 26, etc.), and/or a user interface(s) (e.g., user interface(s) 120). The user interface(s) 120 described herein may include, without limitation, any combination of input and/or output devices that allow an operator to provide operator inputs to the computing system 202 and/or that allow the computing system 202 to provide feedback to the operator, such as a keyboard, keypad, pointing device, buttons, knobs, touch sensitive screen, mobile device, audio input device, audio output device, and/or the like. Additionally, the computing system 202 may be communicatively coupled to one or more position sensors 122 configured to generate data indicative of the location of the implement 10 and/or the vehicle 12, such as a satellite navigation positioning device (e.g., a GPS system, a Galileo positioning system, a Global Navigation satellite system (GLONASS), a BeiDou Satellite Navigation and Positioning system, a dead reckoning device, and/or the like).

In general, the computing system 202 may correspond to any suitable processor-based device(s), such as a computing device or any combination of computing devices. Thus, as shown in FIG. 3, the computing system 202 may generally include one or more processor(s) 204 and associated memory devices 206 configured to perform a variety of computer-implemented functions (e.g., performing the methods, steps, algorithms, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory 206 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory 206 may generally be configured to store information accessible to the processor (s) 204, including data 208 that can be retrieved, manipulated, created and/or stored by the processor(s) 204 and instructions 210 that can be executed by the processor(s) 204.

It should be appreciated that the computing system 202 may correspond to an existing computing device for the implement 10 or the vehicle 12 or may correspond to a separate processing device. For instance, in one embodiment, the computing system 202 may form all or part of a separate plug-in module that may be installed in operative association with the implement 10 or the vehicle 12 to allow for the disclosed system and method to be implemented without requiring additional software to be uploaded onto existing control devices of the implement 10 or the vehicle 12.

In several embodiments, the data 208 may be stored in one or more databases. For example, the memory 206 may include a sensor database 212 for storing data generated by the sensors 102A, 102B, 108, 122. For instance, the field characteristics sensor(s) 102A, 102B may be configured to continuously or periodically capture data associated with a portion of the field. Similarly, the distance sensor(s) 108 may be configured to continuously or periodically capture data associated with the distance between the field characteristics sensor(s) 102A, 102B and the surface of the field. Additionally, the data from the sensors 102A, 102B, 108 may be taken with reference to the position of the implement 10 and/or the vehicle 12 within the field based on the position data from the position sensor(s) 122. The data transmitted to the computing system 202 from the sensors 102A, 102B, 108, 122 may be stored within the sensor database 212 for subsequent processing and/or analysis. It should be appreciated that, as used herein, the term "sensor data 212" may include any suitable type of data received from the sensor(s) 102A, 102B, 108, 122 that allows for the field characteristics (e.g., moisture content, compaction layer depth, etc.) to be accurately analyzed including GPR data, EMI data, distance data (laser line data, infrared data, ultrasonic data, LIDAR data, radar data, and/or the like), GPS coordinates, and/or other suitable type of data.

The instructions 210 stored within the memory 206 of the computing system 202 may be executed by the processor(s) 204 to implement a field characteristics module 214. In general, the field characteristics module 214 may be configured to assess the sensor data 212 deriving from the sensor(s) 102A, 102B, 108, 122 to determine field characteristics (e.g., moisture content, compaction layer depth, etc.) across the field. For instance, as indicated above, the field characteristics data generated by the field characteristics sensor(s) 102A, 102B may be indicative of the field characteristics below the surface of the field. The field characteristics module 214 may use any known correlation (e.g., look-up tables, suitable mathematical formulas, and/or algorithms) between the data generated by the sensor(s) 102A, 102B and field characteristics to determine the field characteristics. Such known correlations may also be stored within the memory 206, or otherwise be accessible to the field characteristics module 214. In some embodiments, the field characteristics module 214 may also determine residue layer thickness based at least in part on the data generated by the distance sensor(s) 108 and adjust analysis of the data generated by the field characteristics sensor(s) 102A, 102B based at least in part on the residue layer thickness (e.g., ignore field characteristic data corresponding to residue layer depth, give less weight to field characteristic data generated where residue layer is thick, and/or the like).

In some embodiments, the field characteristics module 214 may also generate a field characteristics map based at least in part on the field characteristics data generated by the field characteristics sensor(s) 102A, 102B that correlates the field characteristic(s) below the surface of the field to each location within the field.

It should additionally be appreciated that, in some embodiments, the field characteristics module 214 may also be configured to control the sensor(s) 102A, 102B, 108, 122 to generate data. More particularly, the field characteristics module 214 may also be configured to control the sensor(s) 102A, 102B, when the sensor(s) 102A, 102B are GPR sensors, to operate at a plurality of frequencies, such that the data generated by the sensor(s) 102A, 102B is indicative of the field condition (e.g., moisture content) of the field at a plurality of depths, each of the plurality of depths being associated with one of the plurality of frequencies.

Referring still to FIG. 3, in some embodiments, the instructions 210 stored within the memory 206 of the computing system 202 may also be executed by the processor(s) 204 to implement a control module 216. For instance, the control module 216 may generally be configured to initiate or perform a control action based on the monitored orientation of the field characteristics sensor(s) 102A, 102B relative to the surface of the field. For instance, the control module 216 may compare the distance data from the sensor (s) 108 to at least one distance threshold and/or an angular threshold to determine whether the field characteristics sensor(s) 102A, 102B are at the proper distance and/or angular orientation relative to the surface of the field. For example, if the distance between the field characteristics sensor(s) 102A, 102B and the surface of the field determined based at least in part on the distance data generated by the distance sensor(s) 108 is less than a first distance threshold and greater than a second distance threshold, the field characteristics sensor(s) 102A, 102B is within a proper distance range from the surface of the field for determining the field characteristics below the surface of the field. Otherwise, the field characteristics sensor(s) 102A, 102B is not within the proper distance range from the surface of the field for determining the field characteristics below the surface of the field. Similarly, if an angle between the field characteristics sensor(s) 102A, 102B and the surface of the field determined based at least in part on the distance data generated by the distance sensor(s) 108 is less than a certain magnitude of angle, the field characteristics sensor(s) 102A, 102B is at a proper angular orientation relative to the surface of the field for determining the field characteristics below the surface of the field. Otherwise, the field characteristics sensor(s) 102A, 102B is not at a proper angular orientation relative to the surface of the field for determining the field characteristics below the surface of the field. The distance thresholds and/or the angular magnitude range may be stored within the memory 206, or otherwise be accessible to the control module 216.

When the control module 216 determines based on the comparison(s) that the field characteristics sensor(s) 102A, 102B is not within the proper distance range from the surface of the field and/or that the field characteristics sensor(s) 102A, 102B is not at a proper angular orientation relative to the surface of the field for determining the field characteristics below the surface of the field, the control module 216 may perform a control action. For instance, in one embodiment, the control module 216 may control an operation of the sensor actuator(s) 106 to adjust an orientation (e.g., distance and/or angle) of the field characteristics sensor(s) 102A, 102B relative to the surface of the field when the orientation of the field characteristics sensor(s) 102A, 102B relative to the surface of the field is determined to not be the desired orientation. For example, if the distance between the field characteristics sensor(s) 102A, 102B and the surface of the field is greater than the first distance threshold, the control module 216 may control an operation of the sensor actuator(s) 106 to lower the field characteristics sensor(s) 102A, 102B. Conversely, if the distance between the field characteristics sensor(s) 102A, 102B and the surface of the field is less than the second distance threshold, the control module 216 may control an operation of the sensor actuator(s) 106 to raise the field characteristics sensor(s) 102A, 102B. Similarly, if the field characteristics sensor(s) 102A, 102B is at an angle relative to the surface of the field that has a magnitude greater than an angle threshold, then the control module 216 may control an operation of the sensor actuator(s) 106 to adjust the angle of the field characteristics sensor(s) 102A, 102B relative to the surface of the field. In some embodiments, the control module 216 may additionally, or alternatively, control an operation of the user interface(s) 120 to indicate the position or orientation of the field characteristics sensor(s) 102A, 102B relative the surface of the field based at least in part on the distance data.

It should be appreciated that, in some embodiments, the field characteristics module 214 may evaluate the field condition data collected when the field condition sensor(s) 102A, 102B is determined to not be at the proper orientation/ position relative to the surface of the field differently than the field condition data collected when the field condition sensor(s) 102A, 102B is determined to be at the proper orientation/position relative to the surface of the field. For instance, the field characteristics module 214 may weight the field condition data collected when the field condition sensor(s) 102A, 102B is not at the proper orientation/ position relative to the surface of the field with less weight (e.g., to indicate less confidence) than the field condition data collected when the field condition sensor(s) 102A, 102B is at the proper orientation/position relative to the surface of the field. Alternatively, the field characteristics module 214 may ignore the field condition data collected when the field condition sensor(s) 102A, 102B is not at the proper orientation/position relative to the surface of the field and/or control the field condition sensor(s) 102A, 102B to not collect data when the field condition sensor(s) 102A, 102B is not at the proper orientation/position relative to the surface of the field.

Additionally, in some embodiments, the control module 216 may be configured to perform a control action based at least in part on the monitored field characteristics. For instance, the control action, in one embodiment, includes adjusting the operation of one or more components of the implement 10, such as adjusting the operation of one or more of the actuators 60, 62, 64 to adjust the penetration depth of the ground engaging tool(s) 46, 50, 52, 54 and/or adjust the operation of one or more of the drive device(s) 24, 26 to adjust a speed of the implement 10 and/or the vehicle 12 based on the monitored field conditions (e.g., soil moisture, compaction layer depth, etc.) to improve performance of the implement 10 (e.g., prevent plugging and/or reduce compaction). In some embodiments, the control action may include controlling the operation of the user interface 120 to notify an operator of the field conditions (e.g., soil moisture), and/or the like. Additionally, or alternatively, in some embodiments, the control action may include adjusting the operation of the implement 10 based on an input from an operator, e.g., via the user interface 120.

Additionally, as shown in FIG. 3, the computing system 202 may also include a communications interface 218 to provide a means for the computing system 202 to communicate with any of the various other system components described herein. For instance, one or more communicative links or interfaces (e.g., one or more data buses) may be provided between the communications interface 218 and the sensor(s) 102A, 102B, 108, 122 to allow data transmitted from the sensor(s) 102A, 102B, 108, 122 to be received by the computing system 202. Similarly, one or more communicative links or interfaces (e.g., one or more data buses) may be provided between the communications interface 218 and the user interface 120 to allow operator inputs to be received by the computing system 202 and to allow the computing system 202 to control the operation of one or more components of the user interface 120. Moreover, one or more communicative links or interfaces (e.g., one or more data buses) may be provided between the communications interface 218 and the actuator(s) 60, 62, 64, 106 and/or the drive device(s) 24, 26 to allow the computing system 202 to control the operation of one or more components of the actuator(s) 60, 62, 64, 106 and/or the drive device(s) 24, 26.

Referring now to FIG. 4, a flow diagram of one embodiment of a method 300 for monitoring field characteristics within a field is illustrated in accordance with aspects of the present subject matter. In general, the method 300 will be described herein with reference to the implement 10 and the work vehicle 12 shown in FIGS. 1-2, as well as the various system components shown in FIG. 3. However, it should be appreciated that the disclosed method 300 may be implemented with work vehicles and/or implements having any other suitable configurations, and/or within systems having any other suitable system configurations. In addition, although FIG. 4 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 4, at (302), the method 300 may include receiving field characteristics data indicative of at least one characteristic of a field below a surface of the field, the field characteristics data being generated by a field characteristics sensor supported on a vehicle performing one or more passes across the field. For instance, as described above, the computing system 202 may be configured to receive field characteristics data indicative of at least one characteristic (e.g., moisture content, compaction layer depth, etc.) of a field below a surface of the field, where the field characteristics data is generated by a field characteristics sensor(s) 102A, 102B supported on the vehicle 12 and/or on the implement 10 performing one or more passes across the field.

At (304), the method 300 may include receiving distance data generated by at least one distance sensor supported on the vehicle performing the one or more passes, the distance data being indicative of a distance between the surface of the field and the field characteristics sensor. For instance, as discussed above, the computing system 202 may be configured to receive distance data generated by the distance sensor(s) 108 supported on the vehicle 12 and/or on the implement 10 performing the one or more passes, with the distance data being indicative of a distance between the surface of the field and the field characteristics sensor(s) 102A, 102B.

Moreover, at (306), the method 300 may include determining a position of the field characteristics sensor relative to the surface of the field based at least in part on the distance data. For example, as discussed above, the computing system 202 may be configured to determine a position or orientation of the field characteristics sensor relative to the surface of the field based at least in part on the distance data generated by the distance sensor(s) 108.

Additionally, at (308), the method 300 may include initiating a control action based at least in part on the position of the field characteristics sensor relative to the surface of the field. For instance, as described above, the computing system 202 may be configured to initiate a control action based at least in part on the position of the field characteristics sensor relative to the surface of the field. For example, the computing system 202 may be configured to control an operation of the sensor actuator(s) 106 to adjust the position of the field characteristics sensor relative to the surface of the field based at least in part on the determined position of the field characteristics sensor relative to the surface of the field. Alternatively, or additionally, the computing system 202 may be configured to control an operation of the user interface(s) 120 to indicate the position of the field characteristics sensor relative to the surface of the field based at least in part on the determined position of the field characteristics sensor relative to the surface of the field.

It is to be understood that the steps of the method 300 are performed by the computing system 202 upon loading and executing software code or instructions which are tangibly stored on a tangible computer readable medium, such as on a magnetic medium, e.g., a computer hard drive, an optical medium, e.g., an optical disk, solid-state memory, e.g., flash memory, or other storage media known in the art. Thus, any of the functionality performed by the computing system 202 described herein, such as the method 300, is implemented in software code or instructions which are tangibly stored on a tangible computer readable medium. The computing system 202 loads the software code or instructions via a direct interface with the computer readable medium or via a wired and/or wireless network. Upon loading and executing such software code or instructions by the computing system 202, the computing system 202 may perform any of the functionality of the computing system 202 described herein, including any steps of the method 300 described herein.

The term "software code" or "code" used herein refers to any instructions or set of instructions that influence the operation of a computer or computing system. They may exist in a computer-executable form, such as machine code, which is the set of instructions and data directly executed by a computer's central processing unit or by a computing system, a human-understandable form, such as source code, which may be compiled in order to be executed by a computer's central processing unit or by a computing system, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a computing system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An agricultural system for monitoring field characteristics of a field, the agricultural system comprising:

a vehicle configured to perform one or more passes across a field;

a field characteristics sensor supported on the vehicle such that the field characteristics sensor is spaced apart from a surface of the field during the one or more passes across the field, the field characteristics sensor being configured to generate field characteristics data indicative of at least one characteristic of the field below the surface of the field;

a sensor actuator coupled between the field characteristics sensor and the vehicle, the sensor actuator being selectively controllable to move the field characteristics sensor relative to the vehicle;

at least one distance sensor supported on the vehicle, the at least one distance sensor being configured to generate distance data indicative of a distance between the field characteristics sensor and the surface of the field; and a computing system configured to:

receive the distance data; and initiate a control action based at least in part on the distance data.

2. The agricultural system of claim 1, wherein the computing system is further configured to compare the distance to a first distance threshold based at least in part on the distance data, and wherein the computing system is configured to initiate the control action based at least in part on the comparison of the distance to the first distance threshold.

3. The agricultural system of claim 2, wherein the computing system is further configured to compare the distance to a second distance threshold based at least in part on the distance data, the second distance threshold being less than the first distance threshold, and wherein the computing system is configured to initiate the control action based at least in part on the comparison of the distance to the second distance threshold.

4. The agricultural system of claim 1, wherein the computing system is further configured to determine whether the field characteristics sensor is substantially parallel to the surface of the field based at least in part on the distance data, and wherein the computing system is configured to initiate the control action when the field characteristics sensor is not substantially parallel to the surface of the field.

5. The agricultural system of claim 1, wherein the control action comprises controlling a user interface to indicate a position of the field characteristics sensor relative the surface of the field based at least in part on the distance data.

6. The agricultural system of claim 1, wherein the control action comprises controlling an operation of the sensor actuator based at least in part on the distance data.

7. The agricultural system of claim 1, wherein the field characteristics sensor comprises at least one of a ground penetrating radar (GPR) or an electromagnetic induction (EMI) sensor positioned above the surface of the field.

8. The agricultural system of claim 1, wherein the at least one distance sensor comprises at least one of a laser line sensor, an infrared sensor, an ultrasonic sensor, a LIDAR sensor, or a radar sensor.

9. The agricultural system of claim 1, wherein the computing system is further configured to generate a field characteristics map based at least in part on the field characteristics data, the field characteristics map correlating the at least one field characteristic below the surface of the field at each location within the field.

10. The agricultural system of claim 1, further comprising:

an agricultural implement configured to be towed by the vehicle, the agricultural implement having ground engaging tools configured to engage the field during the one or more passes across the field, wherein the computing system is further configured to adjust an operation of at least one of the vehicle or the agricultural implement based at least in part on the field characteristics data.

11. An agricultural method for monitoring field characteristics of a field, the agricultural method comprising:

receiving, with a computing device, field characteristics data indicative of at least one characteristic of a field below a surface of the field, the field characteristics data being generated by a field characteristics sensor supported on a vehicle performing one or more passes across the field;

receiving, with the computing device, distance data generated by at least one distance sensor supported on the vehicle performing the one or more passes, the distance data being indicative of a distance between the surface of the field and the field characteristics sensor;

determining, with the computing device, a position of the field characteristics sensor relative to the surface of the field based at least in part on the distance data; and initiating, with the computing device, a control action based at least in part on the position of the field characteristics sensor relative to the surface of the field.

12. The agricultural method of claim 11, wherein determining the position of the field characteristics sensor relative to the surface of the field comprises comparing the distance to a first distance threshold based at least in part on the distance data, and wherein initiating the control action comprises initiating the control action based at least in part on the comparison of the distance to the first distance threshold.

13. The agricultural method of claim 12, wherein determining the position of the field characteristics sensor relative to the surface of the field further comprises comparing the distance to a second distance threshold based at least in part on the distance data, the second distance threshold being less than the first distance threshold, and wherein initiating the control action comprises initiating the control action based at least in part on the comparison of the distance to the second distance threshold.

14. The agricultural method of claim 11, wherein determining the position of the field characteristics sensor relative to the surface of the field comprises determining whether the field characteristics sensor is substantially parallel to the surface of the field based at least in part on the distance data, and wherein initiating the control action comprises initiating the control action when the field characteristics sensor is not substantially parallel to the surface of the field.

15. The agricultural method of claim 11, wherein initiating the control action comprises controlling a user interface to indicate a position of field characteristics sensor relative the surface of the field based at least in part on the distance data.

16. The agricultural method of claim 11, wherein initiating the control action comprises controlling an operation of a sensor actuator coupled between the field characteristics sensor and the vehicle to move the field characteristics sensor relative to the vehicle based at least in part on the distance data.

17. The agricultural method of claim 11, wherein the field characteristics sensor comprises at least one of a ground penetrating radar (GPR) or an electromagnetic induction (EMI) sensor positioned above the surface of the field.

18. The agricultural method of claim 11, wherein the at least one distance sensor comprises at least one of a laser line sensor, an infrared sensor, an ultrasonic sensor, a LIDAR sensor, or a radar sensor.

19. The agricultural method of claim 11, further comprising generating a field characteristics map based at least in part on the field characteristics data, the field characteristics map correlating the at least one field characteristic below the surface of the field at each location within the field.

20. The agricultural method of claim 11, wherein an agricultural implement is configured to be towed by the vehicle, the agricultural implement having ground engaging tools configured to engage the field during the one or more passes across the field, the method further comprising adjusting, with the computing device, an operation of at least one of the vehicle or the agricultural implement based at least in part on
the field characteristics data.

* * * * *